(12) United States Patent
Shen

(10) Patent No.: US 10,123,694 B2
(45) Date of Patent: Nov. 13, 2018

(54) OPTICAL MEASUREMENT DEVICE AND OPTICAL MEASUREMENT SYSTEM

(71) Applicant: Tzu Chi University, Hualien (TW)

(72) Inventor: Tsu-Wang Shen, Hualien (TW)

(73) Assignee: Tzu Chi University, Hualien (TW)

( * ) Notice: Subject to any disclaimer, the term of this patent is extended or adjusted under 35 U.S.C. 154(b) by 32 days.

(21) Appl. No.: 15/216,960

(22) Filed: Jul. 22, 2016

(65) Prior Publication Data

US 2017/0224209 A1 Aug. 10, 2017

Related U.S. Application Data

(60) Provisional application No. 62/291,441, filed on Feb. 4, 2016.

(51) Int. Cl.
| | |
|---|---|
| A61B 3/14 | (2006.01) |
| A61B 3/103 | (2006.01) |
| G06K 9/00 | (2006.01) |
| A61B 3/00 | (2006.01) |
| G02B 3/14 | (2006.01) |

(52) U.S. Cl.
CPC ............ *A61B 3/103* (2013.01); *A61B 3/0025* (2013.01); *A61B 3/14* (2013.01); *G02B 3/14* (2013.01); *G06K 9/00604* (2013.01)

(58) Field of Classification Search
CPC ......... A61B 3/103; A61B 3/0025; A61B 3/14; G02B 3/14; G06K 9/00604
USPC ........................................ 351/205, 206, 246
See application file for complete search history.

(56) References Cited

U.S. PATENT DOCUMENTS

| | | | | |
|---|---|---|---|---|
| 5,258,791 | A | * 11/1993 | Penney | A61B 3/14 351/208 |
| 5,684,562 | A | * 11/1997 | Fujieda | A61B 3/107 351/211 |
| 2004/0032650 | A1 | * 2/2004 | Lauer | G02B 21/004 359/385 |
| 2006/0158612 | A1 | * 7/2006 | Polland | A61B 3/107 351/206 |
| 2007/0146869 | A1 | * 6/2007 | Lauer | G02B 5/005 359/368 |
| 2009/0002631 | A1 | * 1/2009 | Campbell | A61B 3/107 351/212 |
| 2009/0161090 | A1 | * 6/2009 | Campbell | A61B 3/0091 356/3 |
| 2010/0182567 | A1 | * 7/2010 | Nouchi | A61B 3/0041 351/208 |

(Continued)

*Primary Examiner* — James Greece
(74) *Attorney, Agent, or Firm* — Amin, Turocy & Watson LLP

(57) ABSTRACT

An optical measurement device including a light emitting element, a light pattern generating element and a light source transmission element is provided. The light pattern generating element includes a disk body, at least one round hole penetrating the disk body, at least one round disk embedded in the round hole, and at least two first magnetic elements disposed on the round disk. One end of the light source transmission element has two second magnetic elements. Through the magnetic connection of the first magnetic elements and the second magnetic elements, a chink on the round disk can rotate with the light source transmission element when the light source transmission element rotates. An optical measurement system including the optical measurement device is also provided.

19 Claims, 4 Drawing Sheets

(56) References Cited

U.S. PATENT DOCUMENTS

| | | | |
|---|---|---|---|
| 2011/0286003 A1* | 11/2011 | Ono | A61B 3/102 |
| | | | 356/495 |
| 2015/0168702 A1* | 6/2015 | Harris | G02B 21/08 |
| | | | 850/30 |
| 2016/0206199 A1* | 7/2016 | Blanco | G02B 21/0004 |

* cited by examiner

OPTICAL MEASUREMENT DEVICE AND OPTICAL MEASUREMENT SYSTEM

BACKGROUND

1. Technical Field

This disclosure relates to optical measurement devices and optical measurement systems that are used for eyes, and, more particularly, to an optical measurement device and an optical measurement system that measure a diopter value.

2. Description of Related Art

A conventional optical measurement device that is used to examine eyes includes a tonometer, an ophthalmic refractometer, an ophthalmoscope and a slit lamp device. The ophthalmoscope examines whether an eyeground has pathological changes, such as retinopathy, glaucoma, optic neuritis and macular degeneration. The slit lamp device examines whether a front one-third portion of an eye structure, including the conjunctiva, sclera, cornea, iris, pupil, crystalline lens and Vitreous humor, has pathological changes. The slit lamp, in cooperation with a specific optic lens or accessories, can also examine the eyeground. The ophthalmic refractometer evaluates the diopter of a patient's eyes.

The existing slit lamp device usually comprises a slit lamp and a microscope. In the use of the slit lamp device, a patient has his chin and forehead against a working platform and a jaw holder, respectively, that should be adjustable according to the size of the head of the patient, so as to examine the patient by the device. However, the slit lamp device is bulky and costly. The ophthalmic refractometer is also bulky.

Accordingly, a hand-held slit lamp has come to the market. The hand-held slit lamp has chinks of different sizes that can be used by rotating a chink disk. However, this chink does not rotate with a light splitter, and, as a result, generates a light pattern that does not align with the chink. Therefore, a doctor cannot examine a patient effectively, unless he further adjusts the overall angle or direction of the hand-held slit lamp to control a position where the light pattern is projected, which brings inconvenience to the doctor. Except the ophthalmic refractometer, existing technologies require a patient to stand in front of an eye chart at a certain distance during an eye examining process, and point the opening of an "E" in the eye chart. However, such examining process is not suitable for babies, children or persons who cannot talk properly. Besides, there is still no instrument that can examine the structure of eyes and measure a diopter.

Therefore, how to provide an optical measurement device and an optical measurement system that can not only adjust a chink and the corresponding angle and direction of chink light conveniently, but also measure the diopter of eyes is becoming an urgent issue in the art.

SUMMARY

The present disclosure provides an optical measurement device, comprising: a light emitting element configured to generate measurement light; a light pattern generating element disposed above the light emitting element and configured to receive the measurement light emitted by the light emitting element, the light pattern generating element comprising: a disk body; at least one round hole penetrating two surfaces of the disk body; at least one round disk embedded in the round hole and configured to rotate with respect to the round disk, wherein the round disk has a chink penetrating two surfaces of the round disk and configured for the measurement light to pass therethrough and change a light pattern of the measurement light; and at least two first magnetic elements disposed on two sides of the chink of the round disk, respectively; a light source transmission element disposed above the light pattern generating element and configured to transmit the measurement light with a changed light pattern; and two second magnetic elements disposed at one end of the light source transmission element, wherein each of the at least two first magnetic elements is magnetically connected to corresponding one of the two second magnetic elements for the round disk and the chink to rotate along with rotation of the light source transmission element.

The present disclosure also provides an optical measurement system, comprising: an optical measurement device, comprising: a light emitting element configured to generate measurement light; a light pattern generating element disposed above the light emitting element and configured to receive the measurement light emitted by the light emitting element and change a light pattern of the measurement light; and a light source transmission element disposed above the light pattern generating element and configured to transmit and project the measurement light with a changed light pattern onto an eyeground; an imaging device configured to capture a light pattern image formed through reflection of the measurement light from the eyeground, and convert the light pattern image into first measurement image data; a focal length matching module disposed in front of the imaging device and configured to control clarity of the first measurement image data; and a calculation unit electrically connected with the imaging device and configured to receive the first measurement image data and analyze the clarity of the first measurement image data, the calculation unit being further configured to: if the first measurement image data is not clear, control the focal length matching module to adjust a focal length to generate second measurement image data for the calculation unit to analyze again, and if the first measurement image data is clear, obtain a diopter value according to the focal length adjusted by the focal length matching module that makes the first measurement image data clear.

In an embodiment, the light emitting element is a light emitting diode.

In an embodiment, the first magnetic elements and the second magnetic elements are magnets.

In an embodiment, the optical measurement device further comprises an optical lens disposed at the other end of the light source transmission element and configured to change a path of the measurement light with the changed light pattern.

In an embodiment, the optical lens is a light splitter or a prism.

In an embodiment, a lens set is disposed in the light source transmission element, and converges light passing through the light source transmission element onto the optical lens.

In an embodiment, the calculation unit is a computer, a cellular phone or a tablet computer, and the calculation unit is electrically connected with the imaging device wiredly or wirelessly.

In an embodiment, the imaging device includes a complementary metal oxide semiconductor image sensor or a charge coupled device image sensor.

In an embodiment, the optical measurement system further comprises an aperture component disposed in a path along which the measurement light with the changed light pattern transmitted by the light source transmission element is projected onto the eyeground, and configured to control light quantity of the measurement light with the changed light pattern projected onto the eyeground.

In an embodiment, the focal length matching module is a lens set in a matrix including a plurality of focusing regions having different focal lengths.

In an embodiment, the focal length matching module is a member embedded with a plurality of lenses having different focal lengths, and the member is disposed in front of the imaging device and configured to converge the light pattern image to enter the imaging device by one of the plurality of lenses.

In an embodiment, the focal length matching module comprises at least one electrically controlled motor and a lens set, and wherein the lens set is disposed in front of the imaging device and configured for the light pattern image to pass through the lens set and to be projected onto the imaging device, and the electrically controlled motor is configured to change an overall focal length of the lens set.

In an embodiment, the focal length matching module comprises an electrically controlled motor and a filled lens element, and wherein the filled lens element has a chamber formed by a film, and the electrically controlled motor is configured to fill liquid into the chamber and change a focal length of the filled lens element in accordance with an amount of the liquid.

In an embodiment, the optical lens is configured to rotate about an angle and change a position where the measurement light with the changed light pattern is projected onto the eyeground, and the calculation unit is configured to analyze a relative relation of the angle and the first measurement image data to obtain the diopter value.

In an embodiment, the light pattern generating element further comprising: a disk body; at least one round hole penetrating two surfaces of the disk body; at least one round disk embedded in the round hole and configured to rotate with respect to the disk body, wherein the round disk has a chink penetrating two surfaces of the round disk and configured for the measurement light to pass therethrough and change the light pattern of the measurement light; and at least two first magnetic elements disposed on two sides of the chink of the round disk, respectively.

In an embodiment, two second magnetic elements are disposed at one end of the light source transmission element, wherein each of the two first magnetic elements is magnetically connected to corresponding one of the two second magnetic elements, and when the light source transmission element rotates, the round disk and its chink rotate with the light source transmission element, to allow the measurement light that is transmitted by the light source transmission element and has its light pattern changed to be projected onto the eyeground.

Through the magnetic connection between the light source transmission element and the light pattern generating element of the optical measurement device according to the present disclosure, the direction of the chink in the light pattern generating element rotates with the direction of the optical lens of the light source transmission element, and the light pattern of the measurement light projected onto the eyeground still aligns with the chink and does not change. Therefore, a user has no need to adjust the overall angle or direction of the optical measurement device manually. Besides, under a circumstance that the direction of the optical lens is fixed, the angle of the light pattern of the original measurement light remain unchanged even if the other chinks in the light pattern generating element are changed. Accordingly, a user can perform a measurement process conveniently. According to the present disclosure, the optical measurement system can receive the measurement light reflected by the eyeground to form measurement image data, and analyze whether the measurement image data is clear. If the measurement image data is not clear, the focal length matching module is controlled to adjust a focal length to generate new measurement image data to be analyzed again, until measurement image data that is clear enough is obtained. A diopter value can thus be obtained according to the focal length of the focal length matching module that makes the measurement image data clear. Therefore, the optical measurement system according to the present disclosure has an eyesight measurement function.

BRIEF DESCRIPTION OF DRAWINGS

The disclosure can be more fully understood by reading the following detailed description of the embodiments, with reference made to the accompanying drawings, wherein.

DETAILED DESCRIPTIONS

The following illustrative embodiments are provided to illustrate the disclosure of the present disclosure, these and other advantages and effects can be apparently understood by those skilled in the art after reading the disclosure of this specification. The present disclosure can also be performed or applied by other different embodiments. The details of the specification may be on the basis of different applications, and numerous modifications and variations can be devised without departing from the spirit of the present disclosure.

Figure 1:
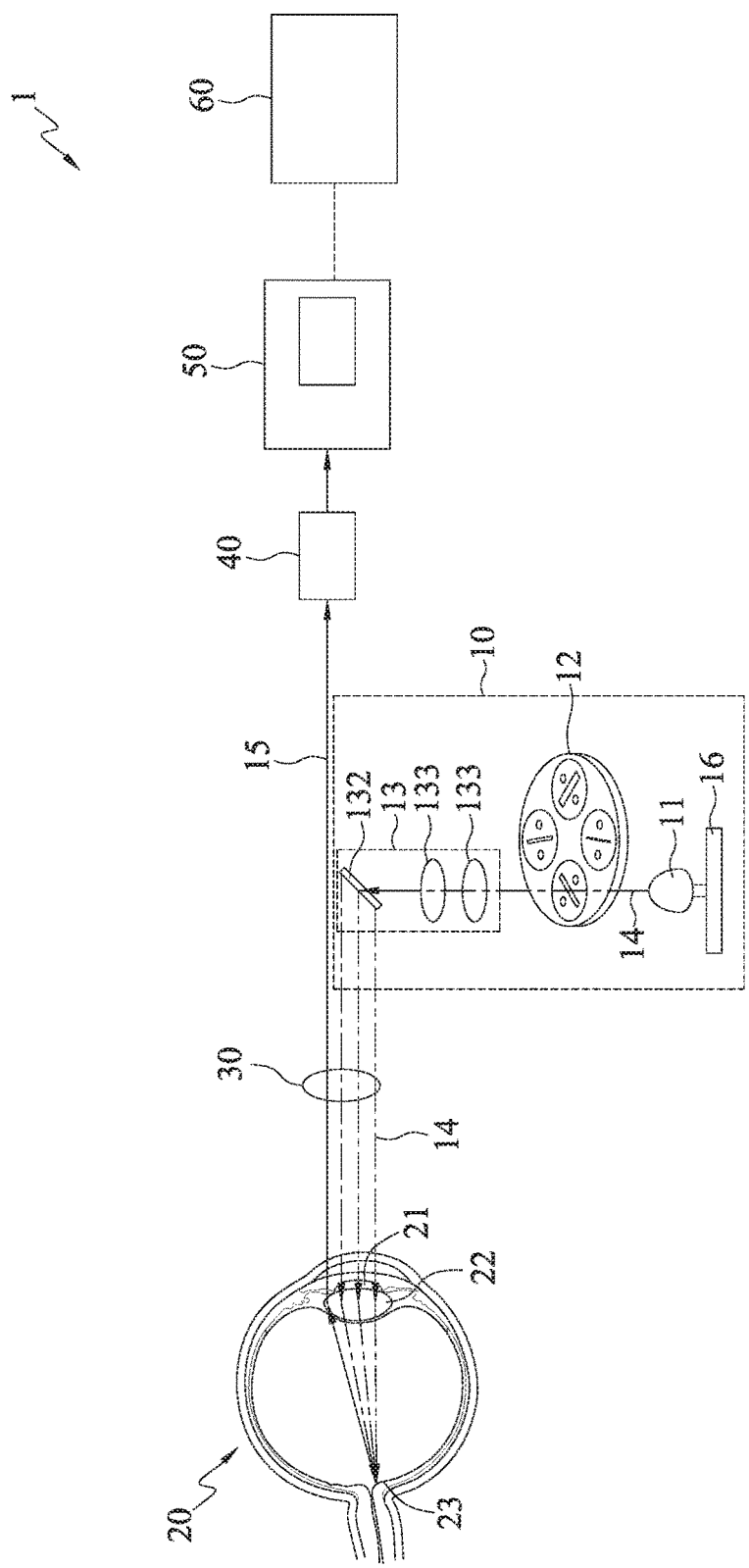
FIG. 1 is a functional block diagram of an optical measurement device and an optical measurement system according to the present disclosure.

Referring to FIG. 1, an optical measurement system 1 according to the present disclosure comprises an optical measurement device 10, an imaging device 50 and a calculation unit 60. In an embodiment, the optical measurement system 1 further comprises an aperture component 30 and a focal length matching module 40.

The optical measurement device 10 comprises a light emitting element 11, a light pattern generating element 12 and a light source transmission element 13. The light emitting element 11 is disposed on a circuit board 16, and generates measurement light 14. In an embodiment, the light emitting element 11 is a light emitting diode that emits red (R) light, green (G) light or blue (B) light. In another embodiment, the measurement light 14 is, but not limited to, visible light or invisible light.

Figure 2:
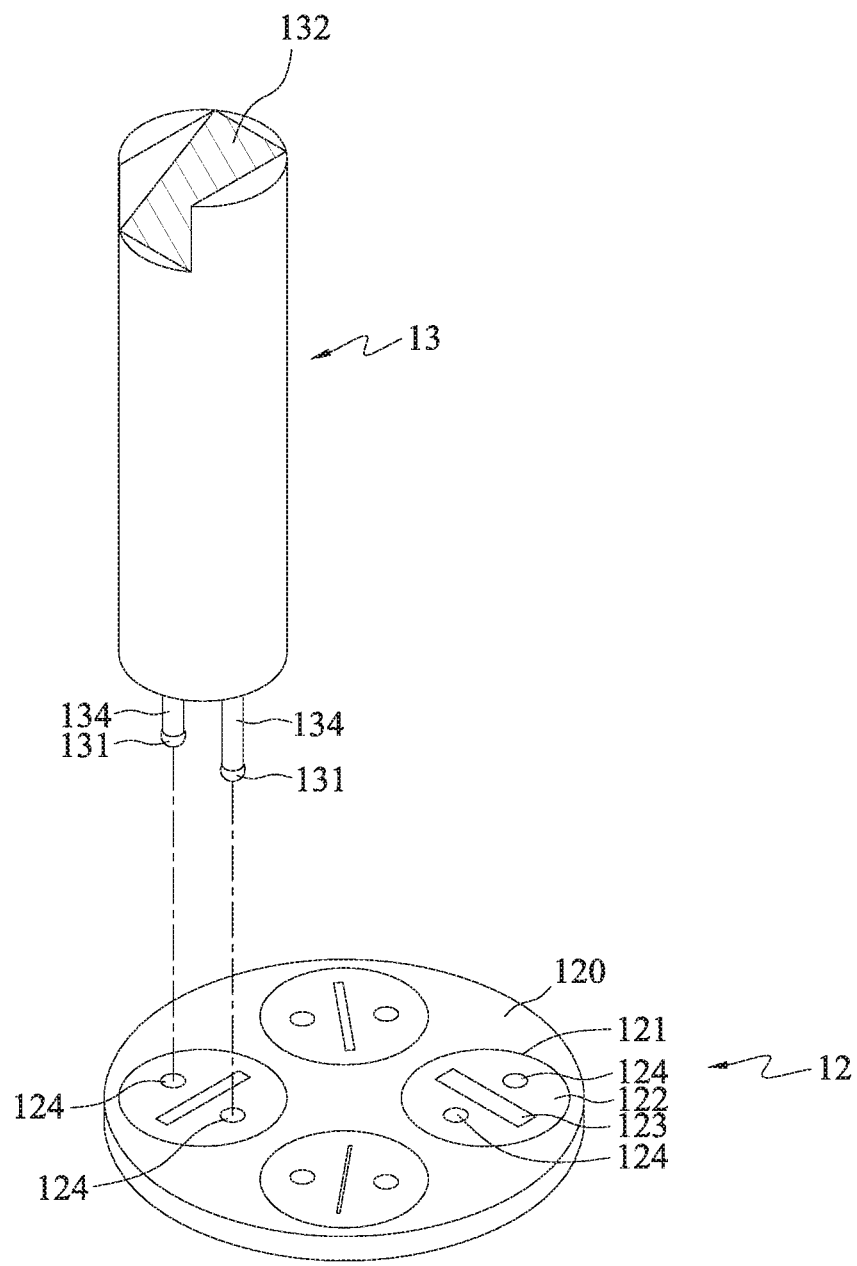
FIG. 2 is a schematic structure diagram of an optical measurement device according to the present disclosure.

The light pattern generating element 12 is disposed above the light emitting element 11, and receives the measurement light 14 emitted by the light emitting element 11. Please also refer to FIG. 2. The light pattern generating element 12 comprises a disk body 120, at least one round hole 121, at least one round disk 122, and at least two first magnetic elements 124.

The round hole 121 penetrates two surfaces of the disk body 120. The round disk 122 is embedded in the round hole 121, and rotates with respect to the disk body 120. In an embodiment, the round hole 121 has a ring-shaped groove, and the round disk 122 has a protrusion corresponding to the ring-shaped groove. After the protrusion of the round disk 122 is embedded into the ring-shaped groove of the round hole 121, the round disk 122 can rotate in the round hole 121. However, the present disclosure does not limit the round disk 122 and the round hole 121 to be combined only by the above design.

The round disk 122 has a chink 123 penetrating two surfaces of the round disk 122. The chink 123 allows the measurement light 14 to pass therethrough, and changes a light pattern of the measurement light 14. In an embodiment, one round disk 122 corresponds to one chink 123, and the chink 123 can be in a variety of shapes, including a rectangle, a square and a circle. The present disclosure does not limit the shape of the chink 123 to be any of the above.

Two first magnetic elements 124 are disposed on two sides of the chink 123 of the round disk 122, respectively. In other words, one round disk 122 has at least two first magnetic elements 124 disposed. In an embodiment, the two first magnetic elements 124 are disposed such that a line connecting the two first magnetic elements 124 is perpendicular to the chink 123. In another embodiment, the two first magnetic elements 124 may be disposed in another manner.

The light source transmission element 13 is disposed above the light pattern generating element 12, and transmits the measurement light 14 that has its light pattern changed. One end of the light source transmission element 13 has two second magnetic elements 131. In an embodiment, the light source transmission element 13 is in a shape of a hollow cylinder, with one end disposed with two supporting members 134, and the second magnetic elements 131 are disposed on ends of the two supporting members 134. In another embodiment, the light source transmission element 13 is disposed on the round disk 122 of the light pattern generating element 12, allowing the first magnetic elements 124 to be magnetically connected to the second magnetic elements 131. In other words, the first magnetic elements 124 and the second magnetic elements 131 are disposed in a direction that they are magnetically attracted to each other. In an embodiment, the first magnetic elements 124 and the second magnetic elements 131 are magnets. Moreover, the present disclosure does not limit the number of the first magnetic elements 124 and the second magnetic elements 131.

The other end of the light source transmission element 13 has an optical lens 132. The optical lens 132 changes a path of the measurement light 14 that has its light pattern changed. In an embodiment, the optical lens 132 is disposed at 45 degrees on one end of the light source transmission element 13, and the path of the measurement light 14 rotates about 90 degrees. A lens set 133 is further disposed in the light source transmission element 13, and converges measurement light 14 onto the optical lens 132. In an embodiment, the optical lens 132 is a light splitter or a prism.

In the optical measurement device 10 according to the present disclosure, when the second magnetic elements 131 of the light source transmission element 13 is magnetically connected to the first magnetic elements 124 on the round disk 122 of the light pattern generating element 12 and the light source transmission element 13 rotates, the round disk 122 and the chink 123 on the round disk 122 are driven to rotate accordingly by a magnetic force. In other words, the chink 123 on the round disk 122 of the light pattern generating element 12 and the optical lens 132 of the light source transmission element 13 rotate in the same direction. Therefore, a light pattern of the measurement light projected onto the eyeground aligns with the chink without change, and a user does not need to adjust the overall angle or direction of the optical measurement device manually. When changing to a different chink, a user rotates the light pattern generating element 12 to break the magnetic connection between the second magnetic elements 131 of the light source transmission element 13 and the first magnetic elements 124 on the round disk 122. Then, when the light pattern generating element 12 keeps rotating and arrives at a next round disk 122, since the light source transmission element 13 does not rotate yet (and is fixed), the second magnetic elements 131 are used to adhere the first magnetic elements 124 on the next round disk 122, such that the chink 123 on the next round disk 122 is driven to rotate in the same direction as the last chink. Therefore, the angle of the light pattern of the original measurement light 14 is not changed, and a user has no need to adjust the overall angle or direction of the optical measurement device manually and can perform a measurement process conveniently. In an embodiment, the optical measurement device 10 can be implemented as a hand-held slit lamp or an ophthalmoscope, and examine the eye structure or eyeground.

The present disclosure uses the optical measurement device 10, together with an aperture component 30, a focal length matching module 40 and an imaging device 50, to constitute the optical measurement system 1 that can acquire measurement image data of an eyeground and use the calculation unit 60 to analyze the measurement image data to obtain a diopter value.

Please refer to FIG. 1 again. The measurement light 14, after passing through the aperture component 30, is projected onto the eyeball 20, and passes through the pupil 21, the crystalline lens 22 and arrives at the eyeground 23 of the eyeball. The measurement light 14 reflected by the eyeground 23 will form a light pattern image 15, passes through the crystalline lens 22 and the pupil 21 to a region outside the eyeball 20, and passes through the aperture component 30. The so-called "light pattern image" is referred to as an image of the light pattern of the measurement light 14 mapped onto the eyeground 23. Therefore, the aperture component 30 is disposed in a path along which the measurement light 14 that is transmitted by the light source transmission element 13 and has its light pattern changed is projected onto the eyeground 23, and controls the light quantity of the measurement light 14 that has its light pattern changed and is projected onto the eyeground 23, and the light quantity of the light pattern image 15 as well, such that the measurement light 14 can be concentrated to pass through the focal length matching module 40 and enter the imaging device 50.

The imaging device 50 captures the light pattern image 15 formed by the measurement light 14 reflected by the eyeground 23, and converts the light pattern image 15 into measurement image data.

The calculation unit 60 is electrically connected to the imaging device 50 to receive the measurement image data and analyze whether the measurement image data is clear. If the measurement image data is not clear, the focal length matching module is controlled to adjust a focal length, so as to generate new measurement image data for the calculation unit to analyze again. If the measurement image data is clear, the focal length matching module obtains a diopter value from the focal length that makes the measurement image data clear. Whether a measurement image data is clear is determined by comparing the light pattern image corresponding to the captured measurement image data with the light pattern image data stored in a database in advance. If they are consistent, the measurement image data is clear; otherwise, the measurement image data is not clear.

In an embodiment, the calculation unit 60 is a computer, a cellular phone or a tablet computer, and the calculation unit 60 is electrically connected to the imaging device 50 wiredly or wirelessly by Bluetooth or WIFI.

In an embodiment, the imaging device includes a complementary metal oxide semiconductor image sensor (CMOS image sensor) or a charge coupled device image sensor (CCD image sensor), and the focal length matching module 40 makes the measurement image data clear. Therefore, the focal length matching module 40, the imaging device 50 and the calculation unit 60 function to analyze a plurality of measurement image data, select the most clearest one of the measurement image data, and calculate a diopter of the eyeball 20 according to the focal length of the focal length matching module that makes the measurement image data clear.

The focal length matching module 40 is illustrated in a variety of embodiments as follows.

Figure 3A:
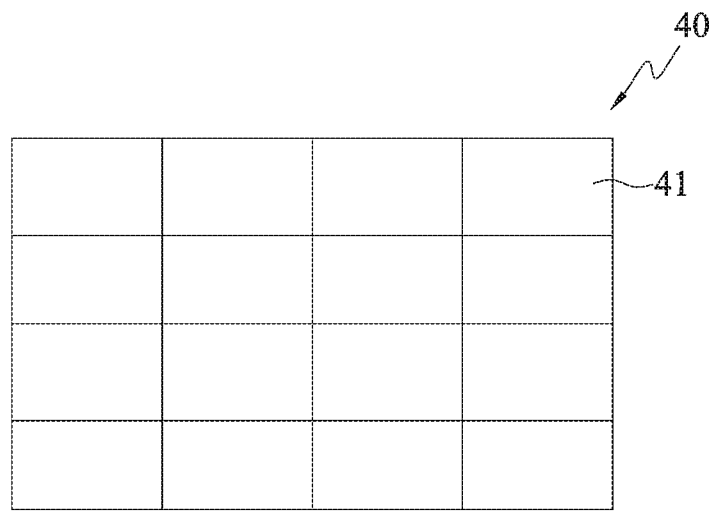
FIG. 3A is a schematic diagram of a focal length matching module of a first embodiment according to the present disclosure.

In an embodiment, as shown in FIG. 3A, the focal length matching module 40 is a lens set in a matrix having a plurality of focusing regions 41 that have different focal lengths. In an embodiment that the eyeball 20 is an abnormal ball (i.e., nearsighted or farsighted), the measurement image data obtained is not clear, and the measurement light 14 cannot focus onto the eyeground 23 accurately. Since the focal length matching module 40 has the focusing regions 41 with different focal lengths, the imaging device 50 can obtain a plurality of measurement image data according to the different focal lengths of the focusing regions 41, and the calculation unit 60 can thus select the clearest one from the plurality of measurement image data and calculate the diopter of the eyeball 20 according to the focal length of the focusing region of the clearest measurement image data.

Figure 3B:
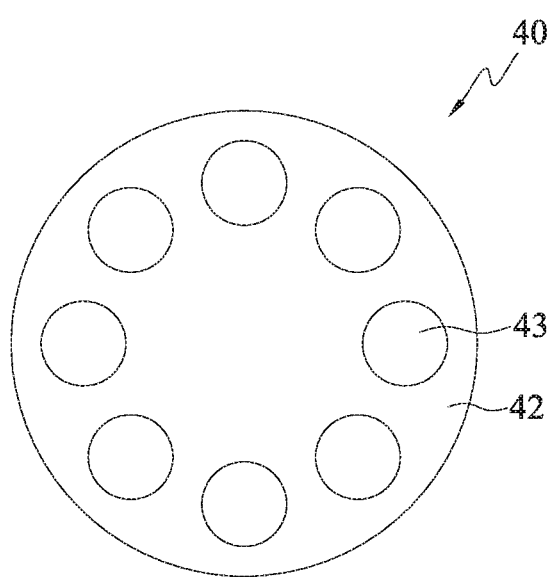
FIG. 3B is a schematic diagram of a focal length matching module of a second embodiment according to the present disclosure.

In another embodiment, as shown in FIG. 3B, the focal length matching module 40 is a round member 42 that has a plurality of lenses 43 disposed in ring-shaped arrangement and embedded in a periphery of the round member 42. The member 42 is disposed in front of the imaging device 50, and uses one of the lenses 43 to converge the light pattern image into the imaging device 50. Similar to the aforementioned, the diopter of the eyeball 20 can be calculated according to the focal length of the lens 43 corresponding to the clearest measurement image data. In an embodiment, the member 42, in addition to be round, can be in other shapes.

Figure 3C:
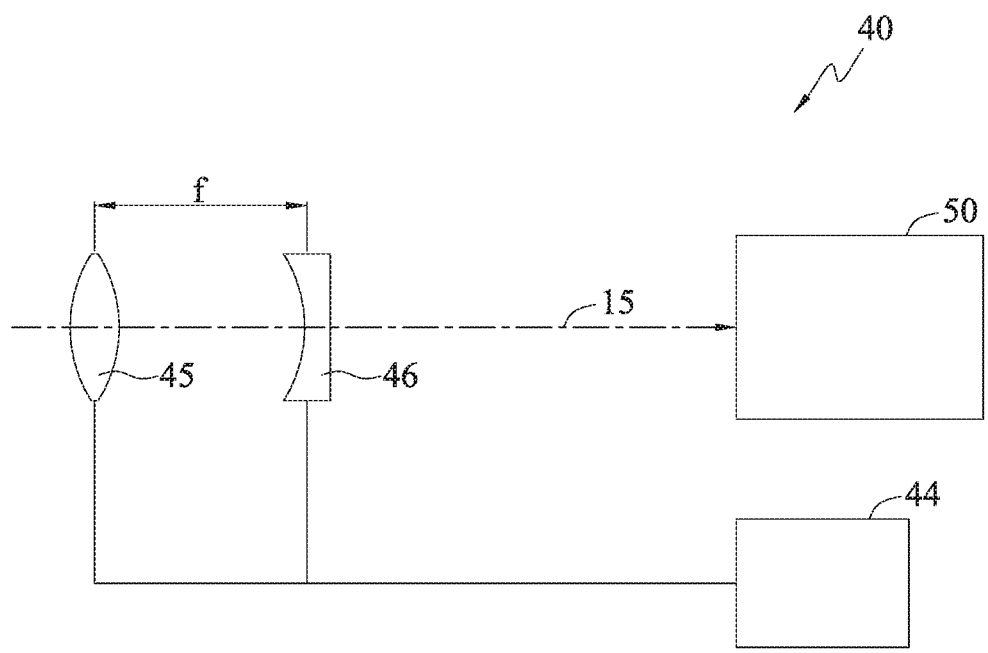
FIG. 3C is a schematic diagram of a focal length matching module of a third embodiment according to the present disclosure.

In yet another embodiment, as shown in FIG. 3C, the focal length matching module 40 comprises at least one electrically controlled motor 44 and a lens set. In an embodiment, the lens set is illustrated by comprising a convex lens 45 and a concave lens 46. In another embodiment, the lens set comprises one or more than one convex lens, concave lens, convex concave lens, concave convex lens or the combination thereof.

The convex lens 45 and the concave lens 46 are disposed in front of the imaging device 50 sequentially, and the light pattern image 15 passes through the convex lens 45 and the concave lens 46 sequentially and is projected onto the imaging device 50. The electrically controlled motor 44 moves the convex lens 45 or the concave lens 46 to change a focal length between the convex lens 45 and the concave lens 46. Through such a focal length moving mechanism, the diopter of the eyeball 20 can be calculated according to the focal length between the convex lens 45 and the concave lens 46 corresponding to the clearest measurement image data. In another embodiment in which the lens set is constituted by a plurality of convex lenses, concave lenses, convex concave lenses and concave convex lenses or the combination thereof, the electrically controlled motor 44, based on actual requirements, moves one or two of these lenses to change the overall focal length of the lens set. The present disclosure does not limit the number of the lenses that the electrically controlled motor moves.

Figure 3D:
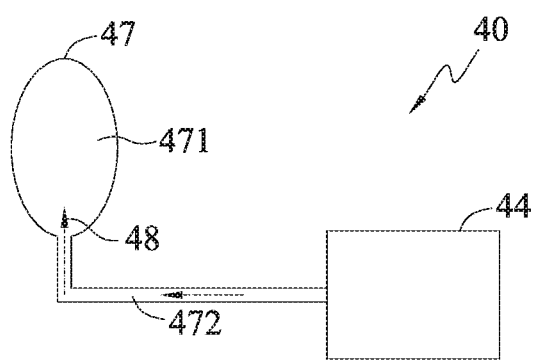
FIG. 3D is a schematic diagram of a focal length matching module of a fourth embodiment according to the present disclosure.
Figure 3D:
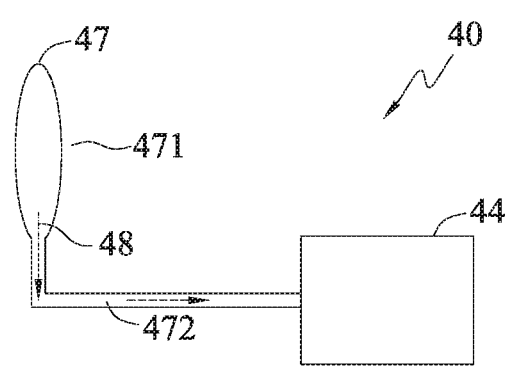

In further another embodiment, as shown in FIG. 3D, the focal length matching module 40 comprises an electrically controlled motor 44 and a filled lens element 47. The filled lens element 47 has a chamber 471 formed by a film. The electrically controlled motor 44 fills liquid 48 into the chamber 471 through a pipe 472. The chamber 471 swells after filled by the liquid 48, and shrinks after the liquid 48 is discharged, and the focal length of the chamber 471 is thus controlled accordingly. In other words, the focal length of the filled lens element 47 can be changed by adjusting the amount of the liquid. Through such a focal length changing mechanism, the diopter of the eyeball 20 can be calculated according to the focal length corresponding to the clearest measurement image data.

In yet further another embodiment in which the optical lens 132 is a light splitter or a prism, the light splitter or the prism rotates and changes the position where the measurement light 14 that has its light pattern changed is projected onto the eyeground. The calculation unit 60 analyzes the rotation angle of the light splitter or the prism and the corresponding measurement image data to generate the diopter value.

According to the present disclosure, the optical measurement system 1 receives the measurement light 14 reflected by the eyeground 23 and forms measurement image data, and the calculation unit 60 further analyzes whether the measurement image data is clear. If the measurement image data is not clear, the calculation unit 60 controls the focal length matching module 40 to adjust the focal length, so as to generate new measurement image data for the calculation unit 60 to analyze again. In other words, the calculation unit 60 has a feedback mechanism regarding the analysis result of the measurement image data, such that the focal length matching module 40 can adjust the focal lengths according to the feedback mechanism, which aims to find out the clearest measurement image data, to allow the focal length matching module to obtain the diopter value according to the focal length of the clearest measurement image data.

In an embodiment, the optical measurement device 10, the aperture component 30, the focal length matching module 40 and the imaging device 50 can be designed as a hand-held device. After the imaging device 50 obtains the measurement image data, the measurement image data can be transmitted to an external calculation unit 60 (e.g., a cellular phone) wiredly or wirelessly, for being further analyzed to generate the diopter of the shot eyeball 20. In addition to the nearsighted and farsighted measurement functions, the optical measurement system according to the present disclosure further has a function to measure astigmatism by the use of a chink 123 in the shape of Union Jack to detect the position where the chink is blurred, and accordingly measures the diopter value of astigmatism. Therefore, the optical measurement system according to the present disclosure has a complete eyesight measurement function.

The foregoing descriptions of the detailed embodiments are only illustrated to disclose the features and functions of the present disclosure and not restrictive of the scope of the present disclosure. It should be understood to those in the art that all modifications and variations according to the spirit and principle in the disclosure of the present disclosure should fall within the scope of the appended claims.

What is claimed is:

1. An optical measurement device, comprising:
  a light emitting element configured to generate measurement light;
  a light pattern generating element disposed above the light emitting element and configured to receive the measurement light emitted by the light emitting element, the light pattern generating element comprising:
    a disk body;
    at least one round hole penetrating two surfaces of the disk body;
    at least one round disk embedded in the round hole and configured to rotate with respect to the round disk, wherein the round disk has a chink penetrating two surfaces of the round disk and configured for the measurement light to pass therethrough and change a light pattern of the measurement light; and
    at least two first magnetic elements disposed on two sides of the chink of the round disk, respectively;
  a light source transmission element disposed above the light pattern generating element and configured to transmit the measurement light with a changed light pattern; and
  two second magnetic elements disposed at one end of the light source transmission element, wherein each of the at least two first magnetic elements is magnetically connected to corresponding one of the two second magnetic elements for the round disk and the chink to rotate along with rotation of the light source transmission element.

2. The optical measurement device of claim 1, wherein the light emitting element is a light emitting diode.

3. The optical measurement device of claim 1, wherein the first magnetic elements and the second magnetic elements are magnets.

4. The optical measurement device of claim 1, further comprising an optical lens disposed at the other end of the light source transmission element and configured to change a path of the measurement light with the changed light pattern.

5. The optical measurement device of claim 4, wherein the optical lens is a light splitter or a prism.

6. The optical measurement device of claim 4, further comprising a lens set disposed in the light source transmission element and configured to converge light passing through the light source transmission element onto the optical lens.

7. An optical measurement system, comprising:
  an optical measurement device, comprising:
    a light emitting element configured to generate measurement light;
    a light pattern generating element disposed above the light emitting element and configured to receive the measurement light emitted by the light emitting element, the light pattern generating element comprises:
      a disk body;
      at least one round hole penetrating two surfaces of the disk body;
      at least one round disk embedded in the round hole and configured to rotate with respect to the disk body, wherein the round disk has a chink penetrating two surfaces of the round disk and configured for the measurement light to pass therethrough and change the light pattern of the measurement light; and
      at least two first magnetic elements disposed on two sides of the chink of the round disk, respectively; and
    a light source transmission element disposed above the light pattern generating element and configured to transmit and project the measurement light with a changed light pattern onto an eyeground;
  an imaging device configured to capture a light pattern image formed through reflection of the measurement light from the eyeground, and convert the light pattern image into first measurement image data;
  a focal length matching module disposed in front of the imaging device and configured to control clarity of the first measurement image data; and
  a calculation unit electrically connected with the imaging device and configured to receive the first measurement image data and analyze the clarity of the first measurement image data, the calculation unit being further configured to:
    if the first measurement image data is not clear, control the focal length matching module to adjust a focal length to generate second measurement image data for the calculation unit to analyze again, and
    if the first measurement image data is clear, obtain a diopter value according to the focal length adjusted by the focal length matching module that makes the first measurement image data clear.

8. The optical measurement system of claim 7, wherein the calculation unit is a computer, a cellular phone or a tablet computer, and the light emitting element is a light emitting diode.

9. The optical measurement system of claim 7, wherein the imaging device is a complementary metal oxide semiconductor image sensor or a charge coupled device image sensor.

10. The optical measurement system of claim 7, further comprising an aperture component disposed in a path along which the measurement light with the changed light pattern transmitted by the light source transmission element is projected onto the eyeground, and configured to control light quantity of the measurement light with the changed light pattern projected onto the eyeground.

11. The optical measurement system of claim 7, wherein the focal length matching module is a lens set in a matrix including a plurality of focusing regions having different focal lengths.

12. The optical measurement system of claim 7, wherein the focal length matching module is a member embedded with a plurality of lenses having different focal lengths, and the member is disposed in front of the imaging device and configured to converge the light pattern image to enter the imaging device by one of the plurality of lenses.

13. The optical measurement system of claim 7, wherein the focal length matching module comprises at least one electrically controlled motor and a lens set, and wherein the lens set is disposed in front of the imaging device and configured for the light pattern image to pass through the lens set and to be projected onto the imaging device, and the electrically controlled motor is configured to change an overall focal length of the lens set.

14. The optical measurement system of claim 7, wherein the focal length matching module comprises an electrically controlled motor and a filled lens element, and wherein the filled lens element has a chamber formed by a film, and the electrically controlled motor is configured to fill liquid into the chamber and change a focal length of the filled lens element in accordance with an amount of the liquid.

15. The optical measurement system of claim 7, further comprising two second magnetic elements disposed at one end of the light source transmission element, wherein each of the at least two first magnetic elements is magnetically connected to corresponding one of the two second magnetic elements for the round disk and the chink to rotate along with rotation of the light source transmission element and for the measurement light transmitted by the light source transmission element with the changed light pattern to be projected onto the eyeground.

16. The optical measurement system of claim 15, wherein the first magnetic elements and the second magnetic elements are magnets.

17. The optical measurement system of claim 15, further comprising an optical lens disposed at the other end of the light source transmission element and configured to change a path of the measurement light with the changed light pattern, wherein the optical lens is a light splitter or a prism.

18. The optical measurement system of claim 17, further comprising a lens set disposed in the light source transmission element and configured to converge light passing through the light source transmission element onto the optical lens.

19. The optical measurement system of claim 17, wherein the optical lens is configured to rotate about an angle and change a position where the measurement light with the changed light pattern is projected onto the eyeground, and the calculation unit is configured to analyze a relative relation of the angle and the first measurement image data to obtain the diopter value.

* * * * *